US00PP36620P3

(12) United States Plant Patent
Ruter

(10) Patent No.: US PP36,620 P3
(45) Date of Patent: Apr. 22, 2025

(54) ***CHAMAECYPARIS* PLANT NAMED 'RutCham1'**

(50) Latin Name: *Chamaecyparis species*
Varietal Denomination: RutCham1

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 135 days.

(21) Appl. No.: 18/234,586

(22) Filed: Aug. 16, 2023

(65) Prior Publication Data

US 2025/0063961 P1 Feb. 20, 2025

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
See application file for complete search history.

*Primary Examiner* — Susan McCormick Ewoldt
(74) *Attorney, Agent, or Firm* — THOMAS | HORSTEMEYER, LLP

(57) ABSTRACT

A new and distinct cultivar of *Chamaecyparis* plant named 'RutCham1', characterized by its good heat tolerance in USDA Hardiness Zone 8 relative to typical *Chamaecyparis pisifera* cultivars; foliage that turns golden in the winter and green in the summer for multi-seasonal interest; and a uniform, pyramidal shape.

2 Drawing Sheets

Botanical designation: *Chamaecyparis* species.
Cultivar denomination: 'RutCham1'.

BACKGROUND OF THE INVENTION

The present invention relates to a new and distinct cultivar of *Chamaecyparis*, botanically known as *Chamaecyparis pisifera*, and hereinafter referred to by the cultivar name 'RutCham1'.

The new *Chamaecyparis* 'RutCham1' is a product of open-pollenated seed from unknown cultivars received in 2013 from Poland (accession record 13-0152, unpatented). The seed was planted in the research field in Watkinsville, Georgia, on Oct. 25, 2014, identified as 3-12. After evaluating the growth habit, it was selected as trial number 2015-1 in 2015.

Asexual reproduction of the new *Chamaecyparis* 'RutCham1' using hardwood cuttings taken during the winter months has been continued in Watkinsville, GA since 2015. Observations of the resulting progeny have shown that the unique features of this new *Chamaecyparis* 'RutCham1' are stable and reproduced true to type in successive generations.

SUMMARY OF THE INVENTION

The new *Chamaecyparis* cultivar 'RutCham1' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Chamaecyparis* cultivar named 'RutCham1'. In combination, these traits set 'RutCham1' apart from all other existing varieties of *Chamaecyparis* known to the inventors.

1. Uniform, pyramidal shape.
2. Foliage turns golden in the winter and green in the summer for multi-seasonal interest.
3. Good heat tolerance as compared to typical *C. pisifera*, which does not perform well in USDA Hardiness Zone 8 and warmer.

Plants of the new *Chamaecyparis* can be compared to similar cultivar *Chamaecyparis pisifera* 'Filifera Aurea' (unpatented) and differ from 'Filifera Aurea' at least in that plants of the new *Chamaecyparis* have more vertical sprays, and branchlets are less pendulous, providing the more uniform, pyramidal shape. Also, the foliage on 'Filifera Aurea' is more threadlike than the foliage of the new *Chamaecyparis* 'RutCham1'.

BRIEF DESCRIPTION OF THE PHOTOGRAPHS

The accompanying, colored photographic illustrations show the overall appearance and distinct characteristics of the new cultivar of *Chamaecyparis* 'RutCham1' showing the colors as true as possible. Colors in the photographs may differ slightly from the color values cited in the detailed botanical description, which accurately describes the colors of the new *Chamaecyparis* 'RutCham1'. The photographs were taken in February 2023 of nine-year-old plants grown outdoors in Watkinsville, Georgia.

Figure 1:
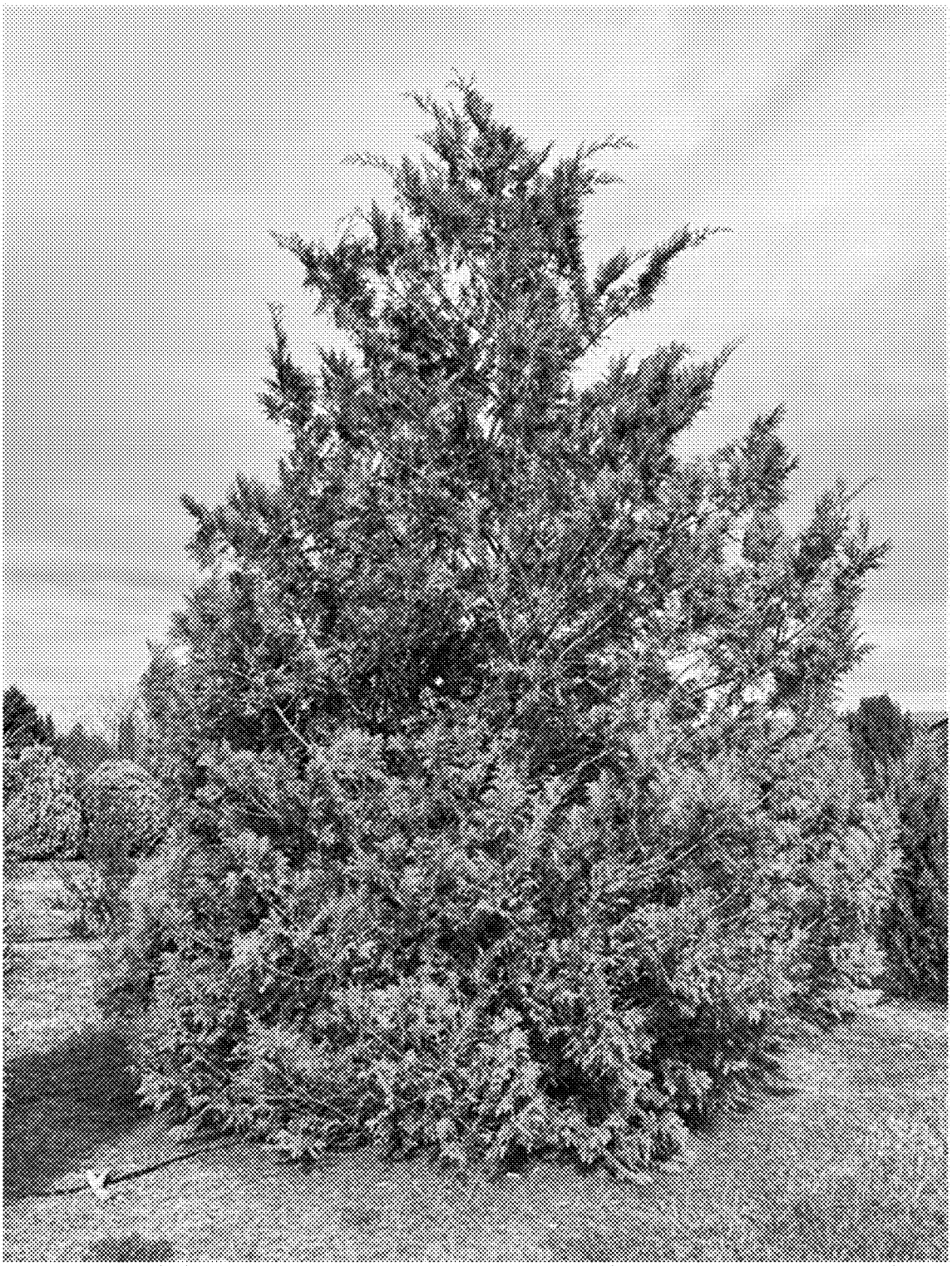

The photograph labeled FIG. 1 depicts a side view of a typical 'RutCham1' plant showing the general form and features, including the upright, pyramidal form.

Figure 2:
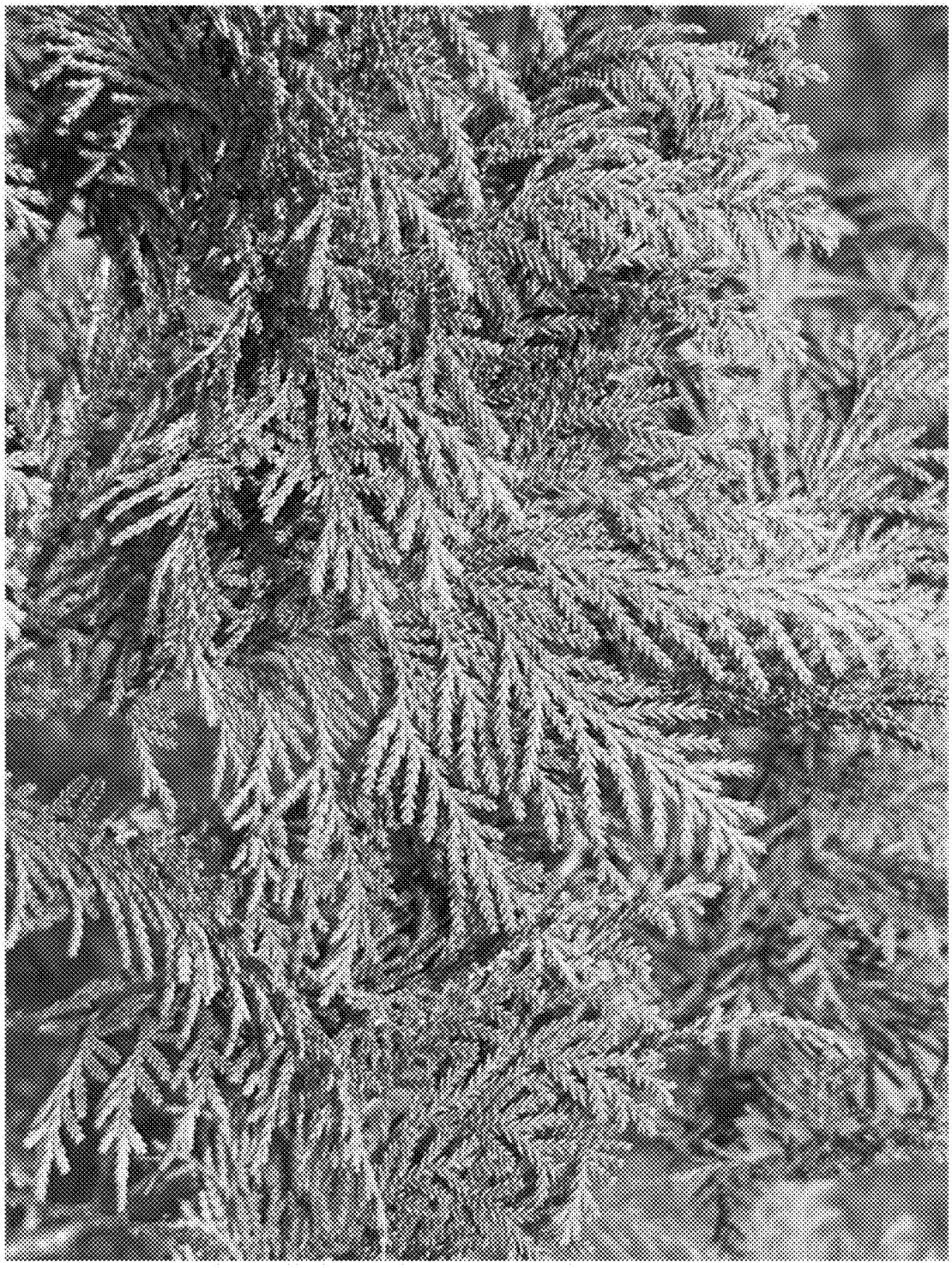

The photograph labeled FIG. 2 depicts a close-up view of the branches and needles of a typical 'RutCham1' plant showing its golden winter foliage.

DETAILED BOTANICAL DESCRIPTION

The following traits have been consistently observed in the original plant of this new variety and in asexually propagated progeny grown in Watkinsville, Georgia, and, to the best knowledge of the inventors, their combination forms the unique characteristics of the new variety 'RutCham1'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England in 2007, except where general terms of ordinary dictionary significance are used.

The aforementioned photographs and following observations, measurements, and values describe plants of the *Chamaecyparis* cultivar named 'RutCham1'. Data were collected from plants that were approximately eight years old and were grown in the ground under outdoor conditions in Watkinsville, GA. The average low temperatures ranged from lows of about 33° F. to 42° F. in the winter, to average high temperatures of about 85° F. to 92° F. in summer.

Botanical classification: *Chamaecyparis* 'RutCham1'.

Commercial classification: Ornamental conifer.

Parentage: Open pollination of unknown *Chamaecyparis*.

Growth and propagation:

*Propagation type.*—Terminal or sub-terminal hardwood cuttings.

*Growth rate.*—Fast, similar to that of *Chamaecyparis pisifera* 'Filifera Aurea' (unpatented) cultivars.

*Root description.*—Usually about 1-5 roots arising from the base of the cuttings.

*Rooting habit.*—Typical for the species, not vigorous.

Plant description:

*Habit.*—Of 10-year plant in field — upright, pyramidal.

*Usage.*—Various uses, including landscaping, ornamental, border, hedge, and mass planting.

*Vigor.*—Moderately vigorous.

*Size of 9-year plant.*—A. Height: from soil level to top of plant, about 20 feet. B. Width: about 11 feet.

*Branch/stem.*—A. Quantity: about one main stems/branches per plant with numerous branches and lateral branches. B. Length: About 12-14 cm. C. Base Diameter: About 1-2 mm at year 1 and about 4-5 mm at year 2. D. Branch angle: year 1 — about 60-75° from center; year 2 — about 15-75° from center. E: Odor (of bruised stem): pleasant resin. F. Internode length: about 5 mm at years 1 and 2. G: Color (RHS): year 1 — Greyed-orange 163B, year 2 — Greyed-green 198C. H: Strength of lateral branches: moderate. I: Pubescence: none. J: Shape: year 1 — flattened, year 2 -— round. K: Texture: medium to coarse.

*Leaf.*—A. Leaf type: scale-like. B. Mature size (L×W): About 2 mm×about 2 mm. C. Arrangement on stem: decussate. D. Aspect: closely appressed to the branchlet. E. Color (RHS): upper — Yellow 7B (winter) and Yellow Green 146C (summer); lower — Yellow Green 144A with white (White 155C) triangular stomatal banding (winter and summer). F. Leaf Number: 1 per scale leaf. G. Apex: acuminate to acute. H. Base: flattened. I. Margin: smooth. J. Shape: facing pair flattened, lateral pair keeled. K. Pubescence: none. L. Venation: linear. M. Texture: rough. O. Odor when crushed: strong resin.

*No male or female cones noted.*—

Weather/temperature tolerance: Plants of the new *Chamaecyparis* have been observed to tolerate about −30° C. without damage in laboratory tests on two-year old wood. Hardiness USDA Zone range 6-9. Plants have not been tested north of USDA Zone 8a.

Disease/pest resistance: To date, plants of the new *Chamaecyparis* have not been observed to have any occurrence of *Passalora* blight (caused by *Passalora sequoiae*) or other foliar diseases in container and field trials.

It is claimed:

1. A new and distinct cultivar of the *Chamaecyparis* plant named 'RutCham1' as illustrated and described herein.

* * * * *